United States Patent [19]

Garren et al.

[11] Patent Number: 4,598,699

[45] Date of Patent: Jul. 8, 1986

[54] ENDOSCOPIC INSTRUMENT FOR REMOVING STOMACH INSERT

[76] Inventors: Lloyd R. Garren; Mary L. Garren, both of P.O. Box 3738, Wilmington, Del. 19807

[21] Appl. No.: 743,000

[22] Filed: Jun. 10, 1985

[51] Int. Cl.⁴ .............................................. A61B 1/00
[52] U.S. Cl. .................... 128/4; 128/303 R; 128/329 R
[58] Field of Search ............... 128/4, 5, 6, 7, 303 R, 128/329 R

[56] References Cited

U.S. PATENT DOCUMENTS

| | | | |
|---|---|---|---|
| 2,034,785 | 3/1936 | Wappler | 128/4 X |
| 3,955,578 | 5/1976 | Chamness et al. | 128/303.15 |
| 4,043,323 | 8/1977 | Komiya | 128/4 |
| 4,134,406 | 1/1979 | Iglesias | 128/303.15 |
| 4,202,338 | 5/1980 | Bitrolf | 128/303.15 |
| 4,372,295 | 2/1983 | Heckele | 128/4 |
| 4,449,518 | 5/1984 | Konomura et al. | 128/4 |
| 4,474,174 | 10/1984 | Petruzzi | 128/4 |
| 4,493,320 | 1/1985 | Treat | 128/303.15 |
| 4,503,855 | 3/1985 | Maslanka | 128/303.15 |

Primary Examiner—William H. Grieb
Attorney, Agent, or Firm—Connolly and Hutz

[57] ABSTRACT

An endoscopic instrument for removing an inflated insert from the stomach cavity of a person being treated for obesity comprises an elongated flexible tube having passageways therein. A holding device at the distal end of the flexible tube is constructed and arranged to grasp and stabilize the inflated stomach insert, and an operator extending through the passageways is provided for manipulating the holding device. A deflating device is also located at the distal end of the flexible tube for puncturing or otherwise causing deflation of the insert after stabilization thereof by the holding device. An operator extending through the passageways is connected to manipulate the deflating device.

4 Claims, 11 Drawing Figures

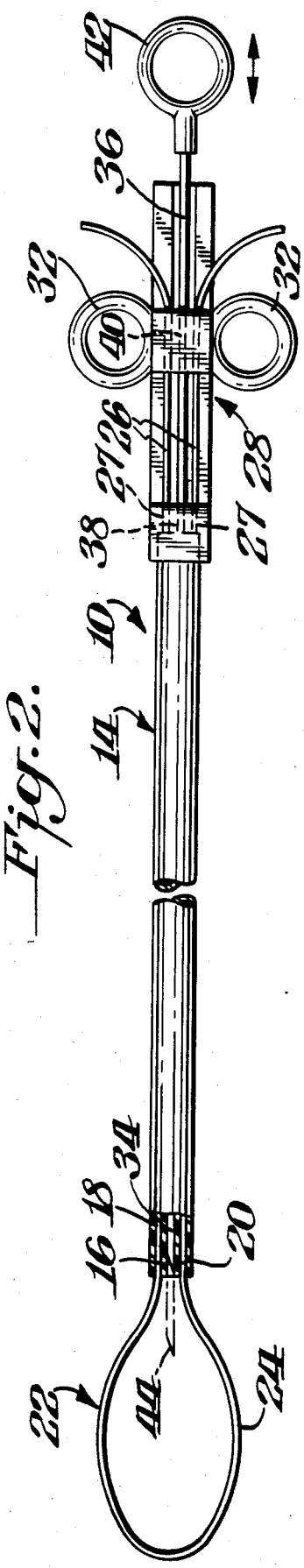
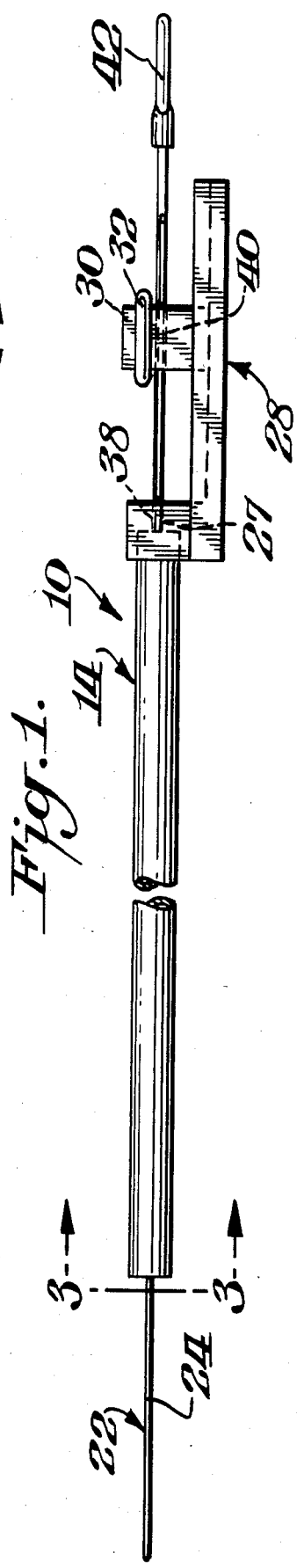
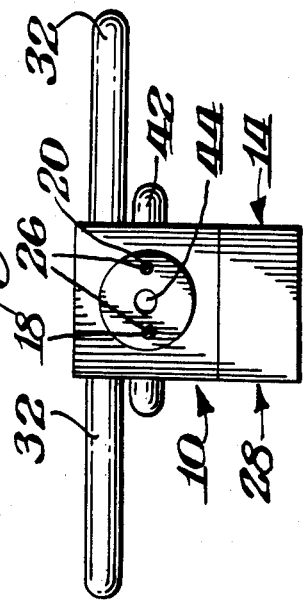

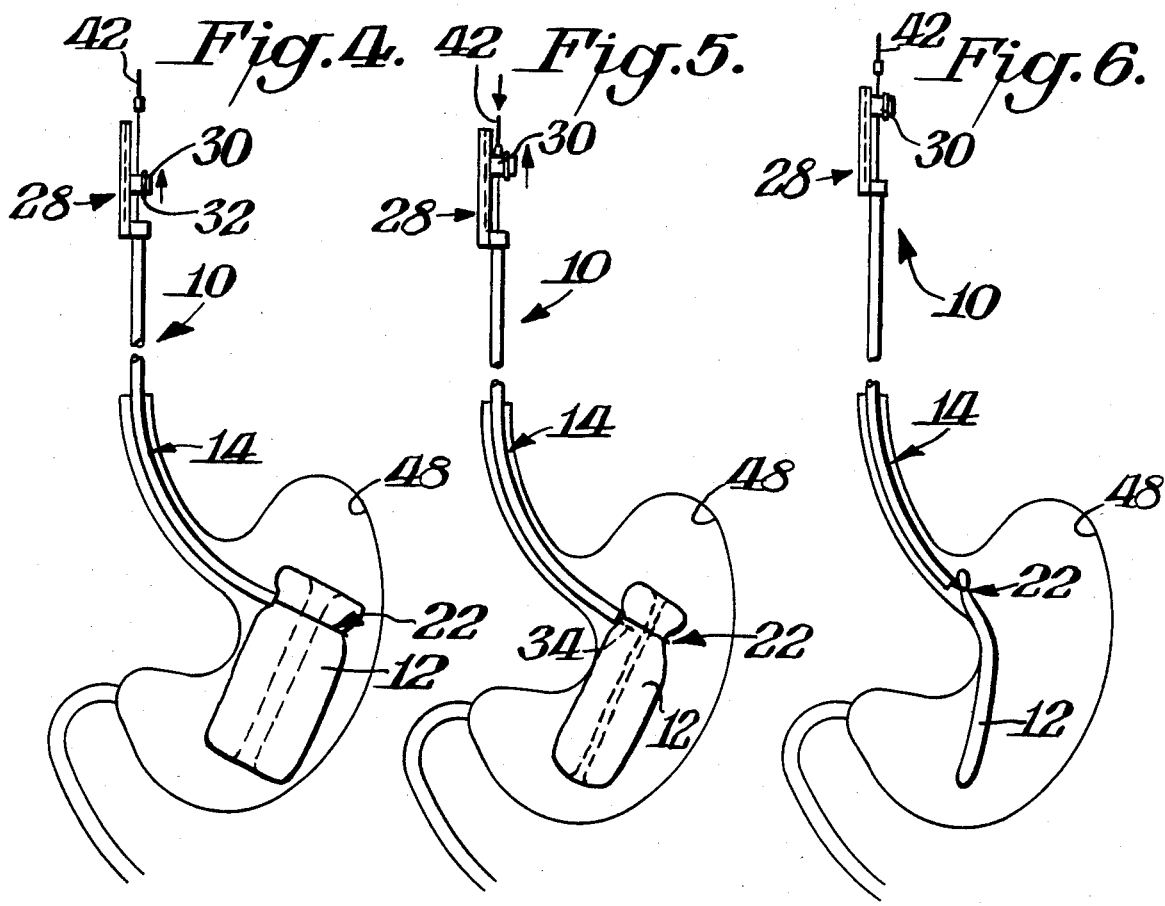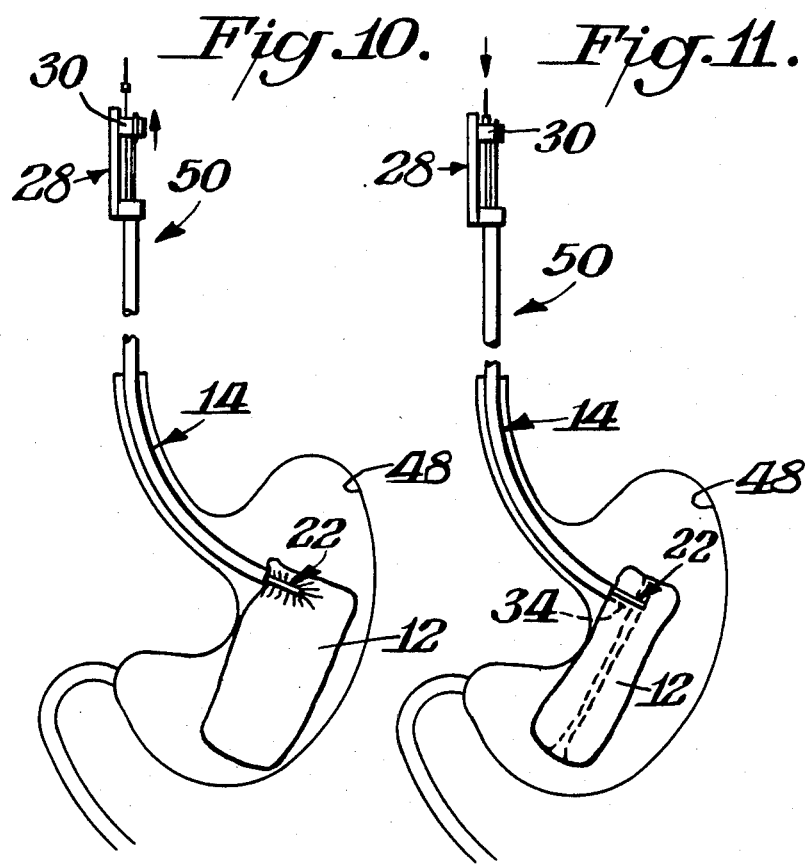

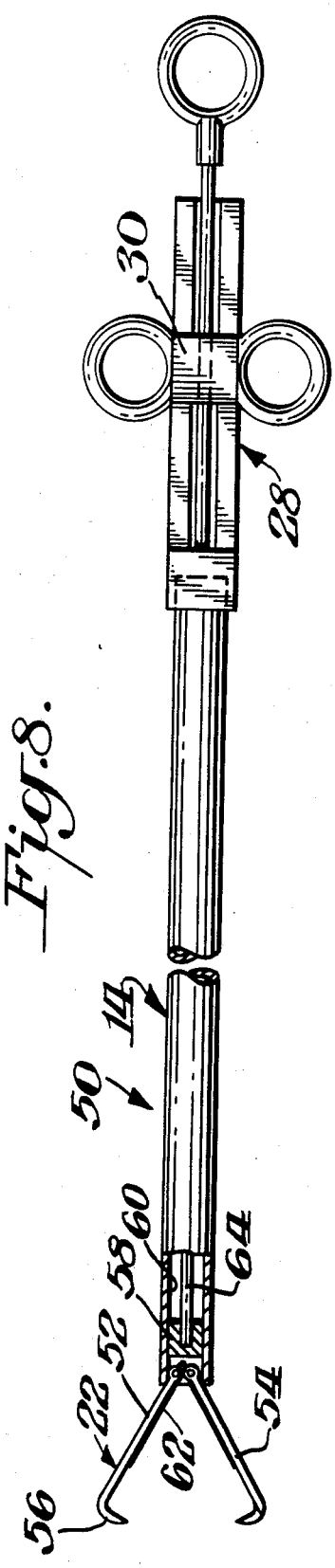
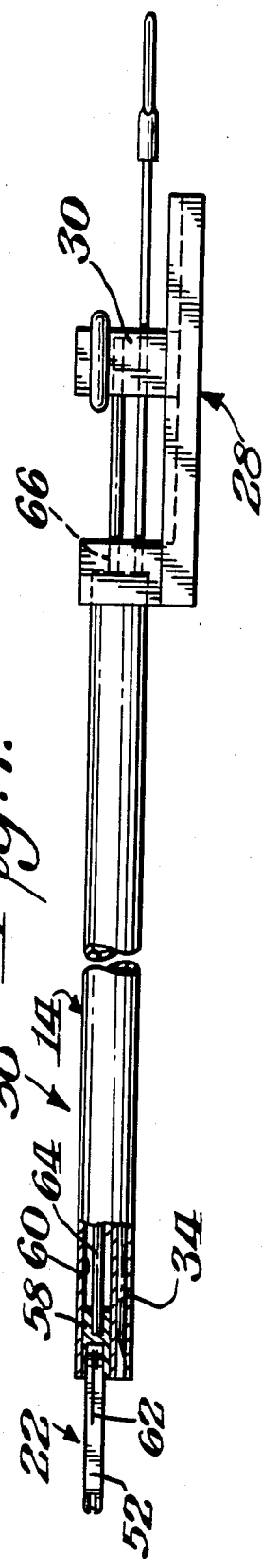
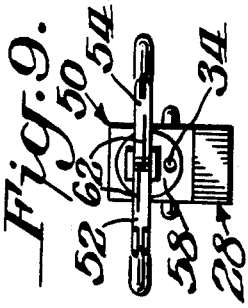

ENDOSCOPIC INSTRUMENT FOR REMOVING STOMACH INSERT

BACKGROUND OF THE INVENTION

The present invention relates to an endoscopic instrument for removing an inflated insert from the stomach cavity of a person being treated for obesity, and more particularly to an endoscopic instrument that functions to stabilize the inflated insert prior to and during deflation thereof to thereby facilitate such removal of the insert.

Extreme obesity is a major illness in the United States and other countries. Its complications include hypertension, diabetes, coronary artery disease, stroke, congestive heart failure, venous disease, multiple orthopedic problems and pulmonary insufficiency with markedly decreased life expectancy. Medical management including dietary, psychotherapy, medications and behavioral modification techniques have yielded extremely poor results in multiple trials. Surgical techniques have proven hazardous to perform in morbidly obese patients and fraught with numerous life threatening postoperative complications.

One non-surgical technique involves the use of an inflated flexible, free-floating and unattached, inflatable insert positioned in the stomach cavity, such as described in U.S. Pat. No. 4,416,267, granted Nov. 22, 1983, and copending application Ser. No. 529,609, filed Sept. 6, 1983. The insert functions to reduce the size of the gastric compartment in a nonoperative manner and has been shown to induce weight loss in a significant percentage of people. While the insert is generally easy to position within the gastric compartment, subsequent removal is sometimes difficult. After the prescribed period of use, removal of the insert is necessary, and the present invention is directed to an instrument for accomplishing such removal. Since the inflated insert is free-floating within the gastric compartment, it is extremely difficult to deflate without first stabilizing the insert. Such stabilization is also difficult due to the general shape of the insert together with the toughness of the material from which it is manufactured and the lubricious characteristic of its outer surface. Efforts to simultaneously grasp and puncture the insert have been far from satisfactory, often resulting in damage to the instrument, particularly when forceps are used.

SUMMARY OF THE INVENTION

Accordingly, it is an object of the present invention to provide an endoscopic instrument for use in removing an inflated stomach insert in an effective and reliable manner.

In accordance with the present invention, an endoscopic instrument for removing an inflated insert from the stomach cavity generally comprises an elongated flexible tube having passageways within the tube. A holding device is positioned at the distal end of the flexible tube and such device is constructed and arranged to grasp and thereby stabilize the inflated insert. An operator connected to manipulate the holding device extends through one of the passageways in the flexible tube to the proximal end of the tube. A deflating device at the distal end of the tube is arranged to penetrate the inflated insert to thereby cause deflation thereof. Another operator connected to manipulate the deflating device extends through one of the passageways in the flexible tube to the proximal end of the tube.

Preferably the holding device comprises a wire snare in the form of a loop constructed and arranged to tightly surround the stomach insert to be removed. Alternatively, the holding device may comprise a pair of jaws movable between open and closed positions, the jaws having teeth at one end thereof and pivotal connections at their opposite ends.

In its simplest configuration the deflating device comprises a relatively rigid element having a sharp end portion slidably mounted for movement into and out of the distal end of the flexible tube. In use, following stabilization of the insert with the holding device, the sharp end portion of the deflating device is urged out of the flexible tube into and through the insert to thereby cause deflation thereof. In its deflated condition, the insert is easily withdrawn out of the stomach through the mouth as the endoscopic instrument is withdrawn.

BRIEF DESCRIPTION OF THE DRAWING

Novel features and advantages of the present invention in addition to those mentioned above will become apparent to those skilled in the art from a reading of the following detailed description in conjunction with the accompanying drawing wherein similar reference characters refer to similar parts and in which:

FIG. 1 is a side elevational view of an endoscopic instrument, according to the present invention;

FIG. 2 is a top plan view of the endoscopic instrument shown in FIG. 1 with portions thereof broken away to show interior details;

FIG. 3 is a sectional view taken along line 3—3 of FIG. 1;

FIG. 4 is a schematic side elevational view illustrating the stomach insert stabilized by the endoscopic instrument of FIGS. 1-3;

FIG. 5 is a schematic side elevational view similar to FIG. 4 illustrating deflation of the insert and retention thereof utilizing the endoscopic instrument of FIGS. 1-3;

FIG. 6 is a schematic side elevational view similar to FIGS. 4 and 5 illustrating the stomach insert in its deflated state retained by the endoscopic instrument of FIGS. 1-3 and being removed from the stomach cavity;

FIG. 7 is a side elevational view of another endoscopic instrument according to the present invention with portions thereof broken away to show interior detail;

FIG. 8 is a top plan view of the endoscopic instrument shown in FIG. 7 with portions thereof broken away to show interior detail;

FIG. 9 is a left end elevational view of the endoscopic instrument shown in FIG. 7 and 8;

FIG. 10 is a schematic side elevational view similar to FIG. 4 but illustrating retention of the insert by the endoscopic instrument of FIGS. 7-9; and FIG. 11 is a schematic side elevational view similar to FIG. 5 but illustrating the endoscopic instrument of FIGS. 7-9.

DETAILED DESCRIPTION OF THE INVENTION

Referring in more particularity to the drawing, FIGS. 1-3 illustrate an endoscopic instrument 10 for use in removing an inflated insert from the stomach cavity of a person being treated for obesity. Inflated, free-floating and unattached stomach inserts used in the treatment of obesity are known in the art from U.S. Pat. No. 4,416,267, granted Nov. 22, 1983, and copending application Ser. No. 529,609, filed Sept. 6, 1983. One such insert 12 is diagrammatically shown in FIGS. 4–6 and 10–11 herein. This insert may be fabricated from medical grade rubber or synthetic rubber-like material, one criteria being that such material be impervious so that the insert is capable of holding a charge of air or other fluid. Moreover, the material should be soft and flexible having significant dynamic strength to resist over-inflation. As such, the finished product will inflate to the manufactured shape and not further. One specific material is TUFTANE, polyester base, thermoplastic polyurethane film, manufactured by the Lord Corp. However, the dynamic strength of the insert coupled with its lubricious outer surface and the fact it is free-floating within the gastric compartment make removal a difficult task without proper instrumentation.

As shown in FIGS. 1–3, endoscopic instrument 10 generally comprises an elongated flexible tube 14 having a central passageway 16 extending therethrough together with a pair of side passageways 18,20. A holding device 22 in the form of a wire snare 24 at the distal end of the flexible tube is constructed and arranged to grasp and thereby stabilize an inflated stomach insert, as explained more fully below. Operator structure 26 in the form of a pair of continuous flexible wires connected to manipulate holding device 22 extend through passageways 18,20 to the proximal end of flexible tube 14.

As shown best in FIGS. 1 and 2, the proximal end of flexible tube 14 is secured to an actuator assembly 28 having a slider 30 mounted thereon for movement toward and away from the flexible tube. Operator wires 26 extend through openings 27 in actuator assembly 28 and are fixed to slider 30 so that movement of the slider toward the tube opens snare 24 and vice versa. Finger grips 32 on the slider facilitate manipulation thereof. A single piece of wire may be suitably fashioned to form the snare and the operator wires.

A deflating device 34 is provided at the distal end of flexible tube 14, and an operator 36 in the form of a single generally stiff wire is connected to the deflating device. Wire operator 36 extends through central passageway 16 in the flexible tube to the proximal end of the tube. Specifically, wire 36 slidably extends through an opening 38 in actuator assembly 28 and an opening 40 in slider 30. A finger ring 42 at the free end of wire 36 facilitates movement of the wire into and out of central passageway 16 in the flexible tube. As shown best in FIG. 2, deflating device 34 comprises a generally rigid element having a sharpened end portion 44 which moves into and out of the distal end of flexible tube 14 upon manipulation of operator wire 36. As explained more fully below, sharp end portion 44 is designed to puncture the stomach insert after the insert is grasped and stabilized by the holding means.

Each of FIGS. 4–6 shows an inflated stomach insert 12 positioned within a gastric compartment 48 of a person being treated for obesity. After the prescribed period of use the insert is removed and the endoscopic instrument of the present invention facilitates such removal. Initially, the distal end of the instrument is inserted through the mouth into the stomach compartment. Next, snare 24 is looped around the insert and slider 30 is moved away from tube 14 in the direction of the arrow in FIG. 4. This procedure functions to grasp and stabilize the insert prior to deflation thereof.

The next step is illustrated in FIG. 5 and primarily involves penetration of the insert with the deflating device 34. This is accomplished by moving the sharpened end portion 44 out of its protected position within the flexible tube. Finger ring 42 is simply urged toward the proximal end of the tube to cause the wire operator to shift the sharpened end portion 44 into and through the stomach insert. Upon puncturing the insert, the air or fluid therein escapes and the insert is significantly reduced in size. Continued outward force is applied to the operator wires 26 to reduce the size of the wire snare so that it complements the reduced size of the deflating insert. This continued force also serves to maintain the insert attached to the instrument.

Finally, as shown best in FIG. 6, the insert is fully deflated and the instrument is withdrawn from the stomach cavity carrying the insert with it. The above procedure may be used in conjunction with a fiberoptic device to assist in locating the insert and instrument prior to grasping the insert with the wire snare.

FIGS. 7–9 illustrate an alternate embodiment of the present invention having many features similar to those of endoscopic instrument 10. In those cases of similarity, the same reference numerals have been used to designate similar parts. Endoscopic instrument 50 of FIGS. 7–9 is different in that the holding device 22 is in the form of a pair of jaws 52,54 having teeth 56 at the free ends thereof. The opposite ends of the jaws are pivoted at 57 to a block 58 slidably mounted within passageway 60 in flexible tube 14. A spring assembly 62 is designed to urge the jaws 52,54 to their open position, as shown in FIG. 8.

A single operator wire 64 is connected to sliding block 58 to manipulate the block relative to the flexible tube. The wire extends through passageway 60 in the tube to the distal end thereof. After passing through opening 66 in actuator assembly 28, wire 64 is connected to slider 30 for movement therewith. Relative movement of the slider to the right as viewed in FIGS. 7 and 8 functions to move the sliding block 58 into tube 14, and such action causes the distal end of the tube to react against jaws 52,54. Such reaction causes the jaws to close as they are retracted into passageway 60 of the flexible tube. Movement of the slider in the opposite direction pushes the jaws out of the tube thereby allowing spring assembly 62 to open them.

Endoscopic instrument 50 also includes a deflating device 34 provided at the distal end of the flexible tube 14 and an operator 36 in the form of a single generally stiff wire is connected to the deflating device. Operation of the deflating device is the same as described above in conjunction with endoscopic instrument 10.

In use, the jaws 52,54 of holding device 22 are retracted to their positions within passageway 60 of flexible tube 14. The sharpened end portion 44 of the deflating device 34 is similarly positioned within its passageway 16. Instrument 50 is then guided into the stomach cavity for removal of the stomach insert therein. As shown best in FIGS. 10 and 11, slider 30 is then urged toward flexible tube 14 which positions the jaws 52,54 in their outward open position, best illustrated in FIG. 8. Next the jaws surround the insert and reverse force is applied to wire operator 64 by slider 30. Such force causes the jaws to partially retract into the flexible tube and as they move in that direction the distal end of the flexible tube acts on the outside surface of the jaws causing them to close tightly around the insert. With the insert so grasped and stabilized, the deflation device is manipulated to puncture the insert and thereby cause reduction of its volume. Continued outward force on slider 30 reduces the size of jaw opening to accompany the reduced size of the insert. When the insert is sufficiently reduced in size, the endoscopic instrument is withdrawn carrying with it the deflated insert.

What is claimed:

1. An endoscopic instrument for removing an inflated insert from a stomach cavity comprising an elongated flexible tube having passageway means therein, holding means at one end of the flexible tube constructed and arranged to grasp an inflated stomach insert, first operator means connected to manipulate the holding means extending through the passageway means to the opposite end of the flexible tube, deflating means at the same end of the tube as the holding means constructed and arranged to penetrate an inflated stomach insert to thereby cause deflation thereof, and second operator means connected to manipulate the deflating means extending through the passageway means to the opposite end of the flexible tube.

2. An endoscopic instrument as in claim 1 wherein the holding means comprises a wire snare in the form of a loop constructed and arranged to tightly surround an inflated stomach insert to be removed.

3. An endoscopic instrument as in claim 2 wherein the holding means comprises a pair of jaws movable between open and closed positions, the jaws having teeth at one end thereof and a pivotal connection at the other end thereof whereby the jaws open and close about the pivotal connection upon manipulation of the first operator means.

4. An endoscopic instrument as in claim 1 wherein the deflating means comprises an element having a sharp end portion slidably mounted for movement into and out of the flexible tube upon manipulation of the second operator means.

* * * * *